(12) United States Patent
Pushpangadan et al.

(10) Patent No.: US 7,344,737 B2
(45) Date of Patent: Mar. 18, 2008

(54) HERBAL COMPOSITION FOR CUTS, BURNS AND WOUNDS

(75) Inventors: Palpu Pushpangadan, Uttar Pradesh (IN); Shanta Mehrotra, Uttar Pradesh (IN); Ajay Kumar Singh Rawat, Uttar Pradesh (IN); Chandana Venkateswara Rao, Uttar Pradesh (IN); Sanjeev Kumar Ojha, Uttar Pradesh (IN); Irfan Aziz, Uttar Pradesh (IN)

(73) Assignee: Council of Scientific and Industrial Research, Rafi Marg, New Delhi (IN)

( * ) Notice: Subject to any disclaimer, the term of this patent is extended or adjusted under 35 U.S.C. 154(b) by 247 days.

(21) Appl. No.: 10/383,070

(22) Filed: Mar. 7, 2003

(65) Prior Publication Data

US 2004/0121027 A1    Jun. 24, 2004

(30) Foreign Application Priority Data

Dec. 20, 2002    (WO)    ........................ PCT/IB02/05561

(51) Int. Cl.
*A61K 36/00* (2006.01)
*A61K 36/28* (2006.01)
*A61K 9/00* (2006.01)

(52) U.S. Cl. ........................ 424/725; 424/764; 424/400
(58) Field of Classification Search ................ 424/725, 424/764; 435/4
See application file for complete search history.

(56) References Cited

U.S. PATENT DOCUMENTS 5,801,192 A * 9/1998 Dumas et al. .............. 514/474
6,299,908 B1 * 10/2001 Rosenstiel .................. 424/618

FOREIGN PATENT DOCUMENTS

JP    3630798009 A  *  4/1988

OTHER PUBLICATIONS

Upadayay et al. (Ethnobotanical study of skin diseases use of medicinia plants of Bihar, pharm.Biol. (36,No. 3, 167-72, 1998).*
Jirovetz et al. (Essential oil analysis of the leaves and root bark of the plant *Clerodendrum infortunatum* used in Ayurvedic medicine, Herba Polonica (1999), 45(2), 87-94).*
Radharishan et al. (Utleria Salicifolia: A new ethnobotanical record from Kerala, India Fitorterapia (1998) vol. 69, No. 5, pp. 403-405).*

* cited by examiner

*Primary Examiner*—Christopher R Tate
*Assistant Examiner*—Randall Winston
(74) *Attorney, Agent, or Firm*—Sughrue Mion PLLC

(57) ABSTRACT

The invention provides a novel herbal composition for treatment of cuts, burns and wounds, the composition comprising plant material selected from *Utleria solicifolia, Jatropha curcas, Clerodendrum infortunatum*, and *Centella asiatica.*

18 Claims, 3 Drawing Sheets

Fig. 1 A: Control (Diplicated Rat – hair removed and marked for creating wound)
Fig. 1 B : Control - Wound of 8 mm created on 0 day and applied ointment

Fig. 1 C : Control - Wound of 8 mm created to group of animals on 0 day and applied ointment
Fig. 2: 3 days treatment of the ointment containing the active plant *Utleria salicifolia*

Fig. 3: **7 days treatment of the ointment containing the active plant *Utleria salicifolia***

HERBAL COMPOSITION FOR CUTS, BURNS AND WOUNDS

TECHNICAL FIELD

The present invention relates to the development of primary health care products. Particularly, the invention provides a novel herbal composition and ointment useful for the treatment of cuts, burns and wounds.

BACKGROUND ART

Wound is disruption of cellular and anatomical continuity of an organism or its parts (Boyd, 1970). The process of cutaneous wound repair is characterized by three overlapping phases involving inflammation, proliferation and the remodeling. After injury, new tissue formation stats with reepethialisation and is followed by granulation tissue formation. The latter process encompasses macrophage accumulation, fibroblast ingrowth, matrix decomposition and angiogenesis (Clark 1996). Inflammation, reepithelization and granulation tissue formation are driven in part by a complex cocktail of growth factors and cytokines, which are released at the site of injury. Although wound healing is essentially a physiologic process, but some chronic wounds exhibit considerable delay in healing. The delayed wound healing may be a consequence of pathologic states associated with immune disorders, diabetes, ischemia, venous stasis, malnutrition, metabolic derangements, burn or gunshot wounds and even ageing. These chronic wounds last much longer, and prolong the care and hospitalsiation time of patients. Trabucchi et al (1988) suggested that oxygen free radicals generated by xenobiotic administration, ischemic-reperfusion or sepsis inhibited the healing of skin or intestinal wounds in rats. Moreover, oxygen free radicals also impaired wound healing by reducing the breaking strength of open-type wound in rats. (Foschi et al 1990). Nishigaki et al (1980) suggested that lipid peroxidation products enter the blood stream at the site of skin burn directly, bringing about damage to cells of remote organs. Chojkier et al. (1989) observed that the product of lipid peroxidation mediate the ascorbic acid induced stimulation of collagen gene expression.

Development of primary health care herbal ointment has been proposed for development of ointment, which covers the antimicrobial, anti-inflammatory, cuts, burns and wounds. For treating wounds the use of solutions of chemical products such as Mercurochrome or quartenary ammonium salts has been suggested for long time. Although widely used, these solutions exhibit the disadvantage of weakening the cell material in which the injury is located and of being only partially effective. Topical antibiotics or sulphonamides have also been used for the same purpose, although these products exhibit numerous indisputable advantages, they sometimes have the disadvantage of extremely low frequency of hypersensitivity reactions apart from a certain toxicity and an irritating action at the point of application, exhibited by some of these products of causing the appearance of a resistant strain of bacteria.

This invention overcomes these disadvantages and relates to a medicinal herbal composition for external use, is easy to use and assists in regeneration of the tissue.

OBJECTS OF THE INVENTION

The primary objective of the invention is to prepare a novel herbal composition for skin protection like wounds, burns and cracks.

Another object is to prepare herbal composition using a combination of medicinal plants to improve skin texture, regenerate dead tissue, pruritis, healing effect on wounds, burns, boils, ulcers and cracks.

Yet another object is to prepare herbal composition having anti-inflammatory effect.

Still another object is to prepare herbal composition having anti-microbial properties.

SUMMARY OF THE INVENTION

In accordance with the present invention provides a herbal composition to heal burns, cuts and wounds. The ingredients of the composition is are obtained from plant materials including *Utleria solicifolia*, which is considered to be a divine plant by tribal people of Kerala and has been used to cure internal wounds and prevent bleeding due to ulcers. Along with this, other plants traditionally used for the treatment of cuts and wounds in the composition are *Jatropha curcas, Clerodendrum infortunatum*, and *Centella asiatica*.

DETAILED DESCRIPTION OF THE INVENTION

Accordingly, the present invention provides a novel wound healing herbal composition useful for the treatment of cuts, burns and wounds, said composition comprising an effective amount of aqueous alcoholic extract of the plants selected from *Jatropha curcas, Clerodendrum infortunatum, Centella asiatica*, and *Utlaria solicifolia*. Other conventional additives may be added to the composition to formulate the same into an ointment or any other form as desired.

The alcoholic extract of the plants comprises:
*Jatropha curcas* 2-4 wt. %,
*Clerodendrum infortunatum* 4-5 wt. %,
*Centella asiatica* 2-4 wt. %, and
*Utlaria solicifolia* 0.5-2 wt. %.

Thus, the present invention provides a herbal composition for the treatment of cuts burns and wounds. This herbal composition has antimicrobial and antifungal properties and gives immediate relief to inflammation unlike the prior art commercial wound healing compositions. Further, the composition is useful for regeneration of the dead cells and connective tissues and in the angiogenesis, matrix synthesis and re-epithelisation.

In an embodiment, the plant extracts may be selected from *Utleria solicifolia, Jatropha curcas, Clerodendrum infortunatum*, and *Centella asiatica*. In yet another embodiment, the plant extracts are obtained: from plant parts selected from rhizome, leaf and aerial parts.

In still another embodiment, the composition may be formulated for topical application such as ointment.

In yet another embodiment, ointment bases are selected from the polyethelene glycol bases, hydroemulsifying bases and H-Bentonite bases.

In still another embodiment, the additives used may be bases such as water-soluble bases.

In yet another embodiment, the water-soluble bases contain: gelatin, tragacanth, Bentonite and pectin, either alone or in combination.

In another embodiment, the extracts of plants used are 50% aqueous alcoholic extracts.

The solvent used for extraction of the plant parts is 50% aqueous alcohol. In another embodiment, the alcohol used is ethanol.

In still another embodiment, the composition has antimicrobial and antifungal properties.

In an embodiment, the additives used in the ointment are selected from the group consisting of polyethylene glycol bases, hydro emulsifying bases and H-Bentonite.

In yet another embodiment, the extracts of the plants are mixed in the ratio *Jatropha curcas* 2-4 wt. %, *Clerodendrum infortunatum* 4-5 wt. %, *Centella asiatica* 2-4 wt. %, and *Utlaria solicifolia* 0.5-2 wt. % along with conventional additives to form an ointment.

In another embodiment, the plant extracts form about 8.5-15% wt of the total composition.

In still another embodiment, the extract of *Utleria solicifolia* is a rhizome extract.

In an embodiment, the composition is used for regeneration of the dead cells and connective tissues.

In another embodiment, the composition assists in angiogenesis, matrix synthesis and reepithelisation.

The composition may be used in excision wound model to monitor wound contraction, wound closure time, tensile strength of the sutures.

In another embodiment, the composition exhibits 100% percent contraction at 4 to 14 days.

In yet another embodiment, the composition exhibits significant increase in the tensile strength at 7 to 15 days.

In still another embodiment, the composition exhibits significant increase in the hydroxyproline content at 7 to 15 days.

In yet another embodiment, the composition exhibits significant increase in wound contraction area at 7 to 15 days.

The composition comprises about 8.5-15% wt. of the total composition and balance being conventional additives. The model used is excision wound model to monitor wound contraction and wound closure time. The model used is incision wound model to monitor tensile strength of the sutures. The composition exhibits percent contraction is 100% at 4 to 14 days in curing of cuts, burns and wounds.

As a result of intensive study conducted by the inventors with the aim of achieving aforementioned objectives, new compositions for topical application were developed employing herbal drugs which are from natural origin, incorporating them into water soluble bases to produce an emollient and soothing effect and non irritant to skin.

Accordingly, in a preferred embodiment, the present invention deals with the topical dosage form, especially ointment. Each composition has been described in detail giving the formula of the ingredients along with the method of preparation.

The invention also provides a method of preparing a herbal composition described earlier wherein the said method comprises:
 a. obtaining plant material from plants selected from *Jatropha curcas, Clerodendrum infortunatum, Centella asiatica* and *Utlaria solicifolia,*
 b. drying the plant material in shade for a period of 4-7 days,
 c. powdering the dried plant material to a coarse powder,
 d. extracting the powdered dried plant material with 40-50% aqueous ethanol at a temperature ranging 25-35° C. for a period of 5-7 days,
 e. concentrating the extract of step (d) at 50°-60° C. under vacuum, and
 f. lyophilizing the concentrated extract for complete removal of solvent and thereby obtaining the herbal composition.

In this method, the powdered plant material to solvent ratio is about 1:8 to about 1:15 The plant parts are selected from the group comprising fruit, rhizome and root parts The first step in the preparation of this compositions involves a process for making, the plant material suitable for formulating into an ointment. The specified portion of the plant is collected and dried under shade at room temperature (25-35° C.) for 60-80 hours or until the material gets dried. The material is then powdered into a fine powder. A specified amount of the powdered material is then extracted exhaustively with 50% aqueous alcohol at room temperature (25-35° C.). Extraction was carried out in a closed container immersing specified amount of the plant material in specified solvent (1:8 to 1:15 ratio) for 4-7 days. At the end of this stage, solvent is decanted and filtered if necessary to make it free from plant debris. The solvent is then concentrated by evaporating under vacuum at less than 40-60° C. The concentrate is then freeze dried to obtain final product in powder form. The final product is then made into a topical dosage form, by using it as an ingredient for making ointments. Suitable ointment bases like watersoluble bases, polyethelene glycol, hydroemulsifying ointment bases and H-Bentonite ointment bases are added to make up the composition. The ointments were prepared by incorporating the extracts into the bases at the specified concentration.

DESCRIPTION OF THE ACCOMPANYING DRAWINGS

FIG. 1A: shows a diplicated rat (hair removed and marked for creating wound)

FIG. 1B: shows animal with wound of 8 mm created and composition of invention applied FIG. 1C: shows control-wound of 8 mm created to group of animals on day 0 and composition of invention applied FIG. 2: Condition after three days of treatment with the composition of invention containing *Utleria salicifolia*

FIG. 3: shows animals after 7 days of treatment with the composition of the invention (containing *Utleria salicifolia*)

EXAMPLE 1

| | |
|---|---|
| *Jatropha curcas* | 3 wt. % |
| *Clerodendrum infortunatum* | 3 wt. % |
| *Centella asiatica* | 3 wt. % |
| *Utlaria solicifolia* | 0.5 wt. % |
| Emulsifying wax | 9.0 g |
| White soft paraffin | 15.0 g |
| Liquid paraffin | 6.0 g |
| Benzoic acid | 0.1% |
| Perfume | q.s. |

*Jatropha curcas, Clerodendrum infortunatum Centella asiatica, Utlaria solicifolia,* were collected in the above ratio and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilised to obtain the extract in powder form. Melt white soft paraffin and emulsifying wax together. Dissolve extracts in water and warm it to the same temp. as that of the melted ingredients of ointment base add the warmed aqueous solution of extracts into the melted mixture, Stir at a temp. not exceeding 40° C. carry out mixing for 30-40 min., till it get solidified. It is used in wound healing, cuts and burns.

EXAMPLE 2

| | |
|---|---|
| Jatropha curcas | 2 wt. % |
| Clerodendrum infortunatum | 4 wt. % |
| Centella asiatica | 2 wt. % |
| Utlaria solicifolia | 2 wt. % |
| White soft paraffin | 32.0 g |
| Bentonite | 13.0 g |
| Sodium laurylsulphate | 0.5 g |
| Purified water | 65.0 |
| Benzoic acid | 0.1% |
| Perfume | q.s. |

*Jatropha curcas, Clerodendrum infortunatum Centella asiatica, Utlaria solicifolia*, were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilised to obtain the extract in powder form. Dissolve the extracts in purified water and warm, add 0.5 gm Sodium Lauryl sulphate. Dissolved extract into bentonite and triturate for 20-30 min., then add white soft paraffin and triturate for 30-40 min. till clicking sound produced to form an ointment.

This composition is used as a antibacterial, antifungal, and in cuts, wounds and thermal burns.

EXAMPLE 3

| | |
|---|---|
| Jatropha curcas | 4 wt. % |
| Clerodendrum infortunatum | 5 wt. % |
| Centella asiatica | 3 wt. % |
| White soft paraffin | 32.0 g |
| Bentonite | 13.0 g |
| Sodium laurylsulphate | 0.5 g |
| Purified water | 65.0 |
| Benzoic acid | 0.1% |
| Perfume | q.s. |

*Jatropha curcas, Clerodendrum infortunatum Centella asiatica* were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilised to obtain the extract in powder form. Dissolve the extracts in purified water and warm, add 0.5 gm Sodium Lauryl sulphate. Dissolved extract into bentonite and triturate for 20-30 min., then add white soft paraffin and triturate for 30-40 min. till clicking sound produced to form an ointment.

It is effective in cuts, wounds and burns.

EXAMPLE 4

| | |
|---|---|
| Jatropha curcas | 3 wt. % |
| Clerodendrum infortunatum | 2.5 wt. % |
| Centella asiatica | 3.5 wt. % |
| Utlaria solicifolia | 0.5 wt. % |
| White soft paraffin | 32.0 g |
| Bentonite | 13.0 g |
| Glycerine | 10 ml |
| Sodium laurylsulphate | 0.5 g |
| Purified water | 65.0 |
| Benzoic acid | 0.1% |
| Perfume | q.s. |

*Jatropha curcas, Clerodendrum infortunatum Centella asiatica, Utlaria solicifolia*, were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilised to obtain the extract in powder form. Dissolved the extract in water and warm, add 0.5 g SLS, bentonite and glycerine triturate together and add dissolved extracts and triturate for 15-20 min, then add white soft paraffin and triturate 3-40 min. till clicking sound produced to form an ointment.

It is used purities, healing effect on wounds, burns, anti-inflammatory, and antimicrobial.

EXAMPLE 5

| | |
|---|---|
| Jatropha curcas | 3 wt. % |
| Clerodendrum infortunatum | 4 wt. % |
| Centella asiatica | 4 wt. % |
| White soft paraffin | 32.0 g |
| Bentonite | 13.0 g |
| Glycerine | 10 ml |
| Sodium laurylsulphate | 0.5 g |
| Purified water | 65.0 |
| Benzoic acid | 0.18% |
| Perfume | q.s. |

*Jatropha curcas, Clerodendrum infortunatum Centella asiatica*, were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilised to obtain the extract in powder form. Dissolved the extract in water and warn, add 0.5 g SLS, Bentonite and glycerine triturate together and add dissolved extracts and triturate for 15-20 min, then add white soft paraffin and triturate 3-40 min. till clicking sound produced to form an ointment.

It is used in boils, ulcer, wounds and cracks as antibacterial and anti-inflammatory.

ADVANTAGES

1. The designed herbal ointment is highly effective in the treatment of cuts, burns and wounds.

2. The scar formation during the healing of the wound is minimized.

3. The cell growth is uniform and leaves behind no scar or protrusion.

TABLE 1

Effect of herbal preparation - Herbal ointment for cuts, burns and wounds on relative mean ± SE organ weights of adult male rats (n = 6)

| Type of treatment | Treatment group | Body weight (gm) | Spleen weight (gm) | Adrenal gland (gm) | Hydroxyproline (mg/gm) | Wound contraction area (sq. mm. %) | Tensile strength (gm) on the 10th day |
|---|---|---|---|---|---|---|---|
| 7 days topical treatment | Control | 162.0 ± 10.5 | 0.696 ± 0.06 | 0.0170 ± 0.006 | 14.15 ± 1.38 | 6.25 ± 1.29 | 544 ± 2.8 |
|  | F1 | 164 ± 10.83 | 0.674 ± 0.037 | 0.0151 ± 0.001 | 16.22 ± 1.06 | 9.75 ± 1.25 | 555 ± 10.8 |
|  | F2 | 168.0 ± 10.36 | 0.438 ± 0.101 | 0.0162 ± 0.002 | 21.92 ± 2.93* | 25.0 ± 1.00* | 658 ± 9.8* |

*significant results were observed.
F1 Composition without *Utleria solicifolia* (without active principle)
F2 Composition with *Utleria solicifolia* (with active principle)

TABLE 2

Percentage closure of excision wound area

| Type of treatment | Treatment group | Percentage contraction |
|---|---|---|
| 4 days tropical treatment | Control | 29.30 ± 0.94 |
|  | Composition | 44.25 ± 1.04 |
| 8 days tropical treatment | Control | 53.12 ± 1.03 |
|  | Composition | 71.52 ± 0.8 |
| 10 days tropical treatment | Control | 65.74 ± 1.04 |
|  | Composition | 89.00 ± 0.08 |
| 14 days tropical treatment | Control | 82.6 ± 0.83 |
|  | Composition | 99.09 ± 0.01 |

Control: without treatment group
Composition: F₂ Composition with *Utleria solicifolia* (with active principle) treated group
Inventors: Pushpangadan, Palpu; Rao, Chandana Venkateswara; Mehrotra, Shanta; Rawat, Ajay Kumar Singh; Irfan, Aziz; and Ojha, Sanjeev Kumar.
Assignee: C.S.I.R.
References cited
4,725,438 February 1988 Leazer
5,487,899 January 1996 Davis
6,261,574 July 2001 Costello Boyd, W. Inflammation and repair. In W. Boyd (Ed.), *Pathology, Structure and Function in Disease* (pp. 76-128). Philadelphia: Febiger. 1970

Clark, R. A. F. Wound repair: Overview and general considerations. In R. A. F. Clark (ED.), *The Molecular and Cellular Biology of Wound Repair* (pp. 3-50). New York: Plenum Press. 1996

Trabucchi, D. F., Musazzi, E., Castoldi, M, Mattia, D. L., Radaelli, D., Marazzi, E., Frazini, M., & Berulsconi, P. A. The effect of oxygen free radicals on wound healing. *Int. J Tissue React* 10, 373-379. 1998

Foschu, D., Castoldi, L., & Radalli, E. Hyaluronic acid prevents oxygen free radical damage to granulation tissue. A study in rat. *Int J Tissue React* 12: 333-339. 1990.

Nishigaki, L, Hagihara, M., Hiramatsu, M., Izawa Y., & Yagi, K. Effect of thermal injury on lipid peroxidation levels of rat *Biochem Med* 24, 185-189. 1990

Chojkier, M., Houglum, K., Herruzo, J. S., & Brenner, D. A. Stimulation of collagen gene expression by ascorbic acid in culturl human fibroblasts. A role for lipid peroxodation. *J Biol Chem* 264, 16957-62, 1989

Anonymous, Indian Pharmacopoeia, Govt. of India, New Delhi. 1996, 1996

Remington. The science and practice of pharmacy, 19th edition, Vol II pp. 1339-1401, 1585-1591, 1995

Palanichamy, S., Amala Bhaskar, E., Bakthavathsalam, R., & Nagarjan, S. Wound healing activity of *Cassia alata*, Fitoterapia, Vol. LXII, NO. 2, pp. 153-156, 1991.

Jamall, I. S., Finelli, V. N., & Que Hee, S. S. A simple method to determine nanogram level of 4-Hydroxyprolinein biological tissues. Analytical Biochemistry, 112, pp. 70-75, 1981

Kakali, S., Mukherjee, P. K., Das, J., Pal, M., & Saha, B. P. wound healing activity of *Leucas lavndulaefolia* Rees. J. Ethnopharmacology, 56, pp 139-144, 1997

The invention claimed is:

1. An herbal composition useful topical for the treatment of skin wounds comprising:
   an alcohol extract of *Utleria salicifolia*;
   an extract of one or more of *Jatropha curcas, Clerodendrum infortunatum*, and *Centella asiatica*; and
   a base composition suitable for topical application,
   said herbal composition being capable of causing at least about 70% contraction of said skin wound after about 10 days of daily topical application of said composition.

2. The herbal composition as claimed in claim 1, comprising an alcohol extract of *Utleria salicifolia* in an amount of from 0.5-2 wt. %, an extract of *Jatropha curcas* in an amount of from 2-4 wt. %, an extract of *Clerodendrum infortunatum* in an amount of from 4-5 wt. %, and an extract of *Centella asiatica* in an amount of from 2-4 wt. %, and the balance being a base composition suitable for topical application.

3. The herbal composition as claimed in claim 1, wherein extracts are extracts of one or more of root, leaves or aerial parts.

4. The herbal composition as claimed in claim 1 wherein the composition is formulated as an ointment.

5. The composition as claimed in claim 4 wherein the ointment is useful for improving skin texture, regenerating dead skin, treating pruritis, and healing effect on wounds, burns, boils, ulcers and cracks.

6. The herbal composition as claimed in claim 4 wherein the ointment is useful for regeneration of connective tissue and acquisition of wound strength.

7. The herbal composition as claimed in claim 1, wherein the composition assists in angiogenesis, matrix synthesis and reepithelisation.

8. The herbal composition as claimed in claim 1 wherein the base composition suitable for topical application is at least one member selected from the group consisting of polyethylene glycol bases, hydro emulsifying bases and H-Bentonite.

9. The herbal composition as claimed in claim 1 wherein the base composition suitable for topical application comprises water-soluble bases.

10. The herbal composition as claimed in claim 9 wherein the water soluble bases are at least one member selected from the group consisting of gelatin, tragacanth, bentonite and pectin.

11. The herbal composition as claimed in claim 1 wherein the alcohol used for extraction is 50% aqueous alcohol.

12. The composition as claimed in claim 1 wherein the alcohol extract of *Utleria salicifolia is a root extract.*

13. The herbal composition as claimed in claim 1 wherein the composition is about 8.5-15% wt. of plant extract and the balance being the base composition suitable for topical application.

14. The herbal composition as claimed in claim 1 wherein the composition exhibits about 100% wound contraction within 14 days of topical treatment.

15. The herbal composition as claimed in claim 1 wherein the composition causes an increase in the wound tensile strength after 7 to 15 days of daily topical application of said composition.

16. The herbal composition as claimed in claim 1 wherein the composition exhibits an increase in the hydroxyproline content.

17. The herbal composition as claimed in claim 1 wherein the composition exhibits an increase in wound contraction area at 7 days.

18. The herbal composition as claimed in claim 1 wherein the composition exhibits antimicrobial and antifungal activity.

* * * * *